United States Patent
Marianne

[11] Patent Number: 6,042,589
[45] Date of Patent: Mar. 28, 2000

[54] REVERSIBLE-ACTION ENDOPROSTHESIS DELIVERY DEVICE

[75] Inventor: Mickaël Marianne, Nancy, France

[73] Assignee: Medicorp, S.A., Cedex, France

[21] Appl. No.: 09/086,535

[22] Filed: May 29, 1998

[30] Foreign Application Priority Data

Mar. 17, 1998 [EP] European Pat. Off. ............. 98200834

[51] Int. Cl.⁷ .................................................. A61F 2/04
[52] U.S. Cl. .......................................................... 606/108
[58] Field of Search ......................... 623/1, 12; 606/108, 606/194, 192, 191

[56] References Cited

U.S. PATENT DOCUMENTS

| | | |
|---|---|---|
| 4,425,908 | 1/1984 | Simon . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,665,906 | 5/1987 | Jervis . |
| 4,681,110 | 7/1987 | Wiktor . |
| 4,743,251 | 5/1988 | Barra . |
| 4,795,458 | 1/1989 | Regan . |
| 4,950,227 | 8/1990 | Savin et al. . |
| 4,954,126 | 9/1990 | Wallsten . |
| 5,026,377 | 6/1991 | Burton et al. . |
| 5,037,427 | 8/1991 | Harada et al. . |
| 5,061,275 | 10/1991 | Wallsten et al. . |
| 5,067,957 | 11/1991 | Jervis . |
| 5,190,546 | 3/1993 | Jervis . |
| 5,197,978 | 3/1993 | Hess . |
| 5,201,901 | 4/1993 | Harada et al. . |
| 5,226,913 | 7/1993 | Pinchuk . |
| 5,354,309 | 10/1994 | Schnepp-Pesch et al. . |
| 5,395,390 | 3/1995 | Simon et al. . |
| 5,405,377 | 4/1995 | Cragg . |
| 5,480,423 | 1/1996 | Ravenscroft et al. . |
| 5,540,712 | 7/1996 | Kleshinski et al. . |
| 5,540,713 | 7/1996 | Schnepp-Pesch et al. . |
| 5,554,181 | 9/1996 | Das . |
| 5,562,725 | 10/1996 | Schmidt et al. . |
| 5,562,728 | 10/1996 | Lazarus et al. . |
| 5,575,818 | 11/1996 | Pinchuk . |
| 5,597,378 | 1/1997 | Jervis . |
| 5,630,840 | 5/1997 | Mayer . |
| 5,643,278 | 7/1997 | Wijay . |
| 5,643,339 | 7/1997 | Kavteladze et al. . |
| 5,645,559 | 7/1997 | Hachtman et al. . |
| 5,647,857 | 7/1997 | Anderson et al. ...................... 604/264 |
| 5,674,277 | 10/1997 | Freitag . |
| 5,695,499 | 12/1997 | Helgerson et al. . |
| 5,741,326 | 4/1998 | Solovay ...................................... 623/1 |
| 5,741,333 | 4/1998 | Frid . |
| 5,769,817 | 6/1998 | Burgmeier ............................... 604/96 |
| 5,782,855 | 7/1998 | Lau et al. ................................. 606/194 |
| 5,833,657 | 11/1998 | Reinhardt et al. ....................... 604/96 |
| 5,843,090 | 12/1998 | Schuetz ................................... 606/108 |
| 5,910,145 | 6/1999 | Fischell et al. ......................... 606/108 |
| 5,957,930 | 9/1999 | Vrba ....................................... 606/108 |

FOREIGN PATENT DOCUMENTS

| | | |
|---|---|---|
| 0705576 | 9/1995 | European Pat. Off. . |
| 0730848 | 2/1996 | European Pat. Off. . |
| 0740928 | 3/1996 | European Pat. Off. . |
| 0744164 | 5/1996 | European Pat. Off. . |
| WO 1205743 | 9/1970 | United Kingdom . |
| WO 9219310 | 11/1992 | WIPO . |
| WO 9530385 | 11/1995 | WIPO . |
| WO 9531945 | 2/1996 | WIPO . |
| WO 9713475 | 4/1997 | WIPO . |
| WO 9717899 | 5/1997 | WIPO . |
| WO 9717914 | 5/1997 | WIPO . |

*Primary Examiner*—Jeffrey A. Smith
*Attorney, Agent, or Firm*—Roylance, Abrams, Berdo & Goodman, L.L.P.

[57] ABSTRACT

A reversible-action endoprosthesis delivery device (1) comprising an axially extending inner tube (8) surrounded by an outer sheath (16) comprising remote-activated retaining device (20) able to maintain or release the endoprosthesis (7) in a fixed axial relationship relative to the inner tube (8) so that up to the end of the placement procedure, the endoprosthesis (7) can be withdrawn and replaced in a more suitable position.

11 Claims, 3 Drawing Sheets

REVERSIBLE-ACTION ENDOPROSTHESIS DELIVERY DEVICE

DESCRIPTION

The invention concerns devices for the placement of luminal endoprostheses in animal body vessels.

In particular, it relates to such a device for the deployment and retraction of a stent, particularly a self-expanding stent.

Advance in angioplasty now results in a particular attention to be given to the precise positioning of endoprosthesis in vessels to be cured. This is particularly true for small vessels.

BACKGROUND OF THE INVENTION

Several attempts have already been made to achieve the possibility of controlling the position of a stent in a delivery device during the placement operation, before its full length becomes radially expanded.

U.S. Pat. No. 5,026,377 discloses a stent delivery device for a self-expanding stent such as the one disclosed in U.S. Pat. No. 4,665,771. The proximal end of the stent to be released is fastened to a central pusher of the device either by an adhesive, or by a local widening of this pusher.

WO 96/13228 discloses a stent delivery device provided with a soft "recapture sleeve"—generally bearing crossed grooves—located on the central pusher of the device in order to prevent axial displacement of a self-expanding stent relative to the pusher before a given fraction of the length of the stent has been allowed to expand.

In practice, however, these devices do not provide fully reliable results.

Just before its deployment in the vessel, the stent is located inside a chamber toward the distal end of the delivery device. Once the stent has been partially deployed and hence allowed to expand, it places itself against the interior wall of the vessel. It proves difficult to force it back into the chamber. Indeed, instead of entering back the chamber, the stent is often ripped out of the end of the delivery device and thus can no longer be displaced without being destroyed or removed by surgery.

Furthermore, the recapture means of the devices according to the state of the art add to the radial cumbersomeness of the delivery device.

There has therefore been a strong need for a space-saving and efficient reversible-action endoprosthesis delivery device.

BRIEF SUMMARY OF THE INVENTION

A precise positioning of the stent requires a precise control of its position via the pusher, whatever the solicitations the stent is subjected to.

Remotely activable retaining means have now been developed, allowing the possibility of entering vessels of small diameter, a strong retaining effect being produced at will when the proximal end of the delivery device carrying the stent has been driven up to the place to be cured.

The subject of the invention is a reversible-action endoprosthesis delivery device extending between a distal end and a proximal handling end, comprising an axially extending inner tube surrounded by an outer sheath, the inner tube comprising, near its distal end, a chamber able to enclose an expendable endoprosthesis in a radially contracted state, the inner tube being axially movable relative to the outer sheath. This device is characterised in that it comprises remote-activated retaining means able, at will, to maintain the endoprosthesis in a given axial relationship in relation to the inner tube and to release same.

According to a preferred embodiment, the remote-activated retaining means comprises an inflatable balloon fixed to the inner tube, this balloon being connected to pressure means placed at the proximal end of the delivery device.

The inflatable balloon is preferably placed near the proximal part of the chamber.

The balloon is advantageously able to be inflated up to a diameter corresponding to the diameter of a body vessel.

Preferably, the device is able to enclose a self-expanding endoprosthesis and particularly an endoprosthesis made of a braid of shape-memory alloy.

The endoprosthesis con also comprise a balloon-expandable stent.

The outer sheath is preferably reinforced by a multiwire braiding, advantageously of metal wires.

BRIEF DESCRIPTION OF THE DRAWINGS

Other advantages of the invention will become apparent when referring to the description hereafter of several embodiments, given as non-limiting examples, reference being made to the appended drawings wherein.

DETAILED DESCRIPTION OF THE SEVERAL VIEWS

Figure 1:
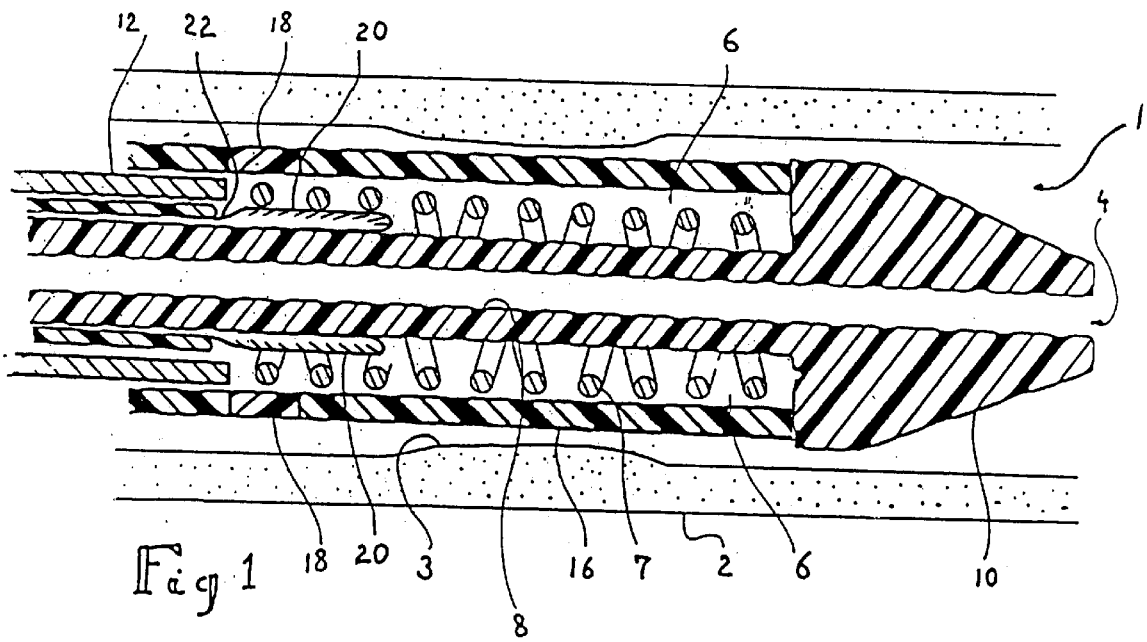
FIG. 1 is a diagrammatic view of a cross-section of the distal part of one embodiment of a device according to the invention.

On FIG. 1, a delivery device 1 according to the invention has been introduced, according to a known procedure, up to a lesion 2 to be cured in a body vessel 3, in the present case a stenosis in an artery 3.

The distal end 4 of the device comprises a chamber 6 wherein an expandable endoprosthesis—represented here as a self-expanding stent 7—has been inserted in a radially contracted state.

The chamber 6 extends around an inner tube 8, between an atraumatic tip 10 and a stent pusher 12. An axial lumen 14 allows the whole delivery device 1 to be driven along a guide wire (not shown).

The chamber 6 is closed by an outer sheath 16 which is axially movable at will relative to the inner tube 8.

The optimal position of the stent 7 after release and expansion can be carefully checked before starting the release process thanks to the presence of radio-transparent markers 18 embedded in the otherwise radio-opaque outer sheath 16.

The delivery device 1 according to the invention also comprises a remote controlled retaining device, that in the present embodiment comprises an inflatable micro-balloon 20 connected to pressure means (not represented) placed at the proximal end of the delivery device 1.

During the insertion steps, the micro-balloon 20 remains in a deflated state, this having virtually no influence on the diameter of the device 1, which can be inserted into very thin vessels 3.

The supposedly optimal position of the device for the deployment of the stent being determined, the micro-balloon 20 is slightly inflated, causing the proximal end of the stent 7 to be firmly locked in place with respect to the inner tube 8.

Figure 2:
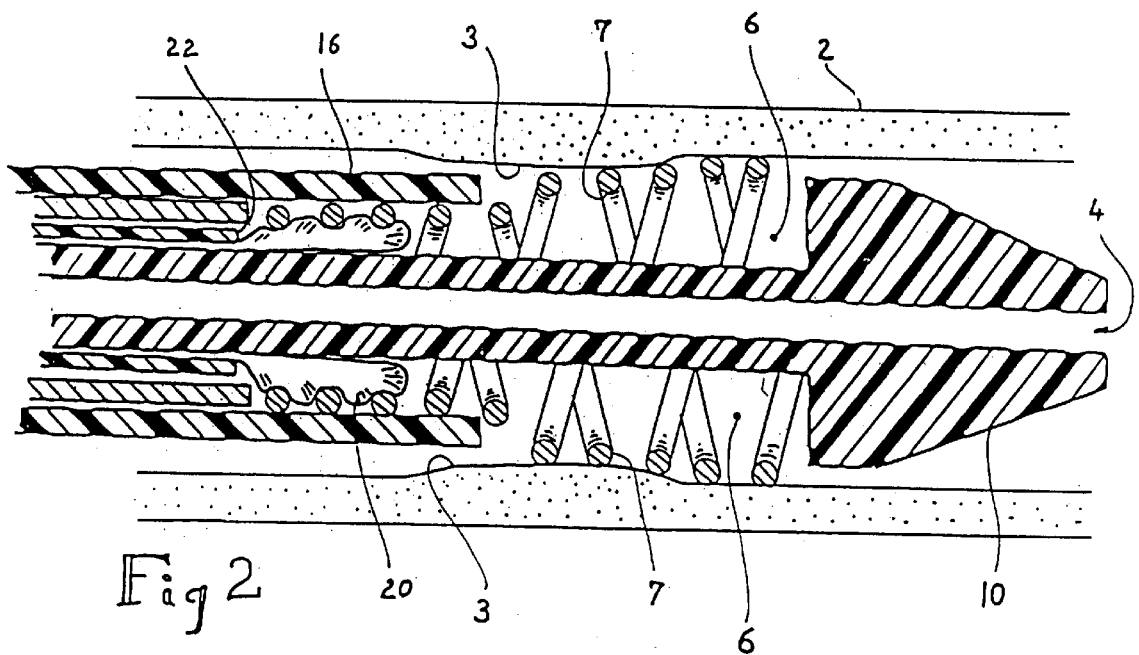
FIG. 2 is a diagrammatic view of the device of FIG. 1 at an early stage of the deployment operation.

The outer sheath 16 can now be moved backwards, as represented on FIG. 2, uncovering the distal end of the stent 7 which expends radially either because of its own resilience, or due to the change of temperature it undergoes.

This stage is critical for most of the delivery devices of the known art which are supposed to have the possibility of forcing back the stent into its chamber.

Indeed, as soon as the stent is deployed, it becomes anchored to the inner wall of vessel and it thus exerts on the outer sheath of the device a resistance sufficient to cause its proximal end to be ripped out of the still closed proximal part of the chamber 6.

This effect is dramatically increased when the stent is a self-expanding stent, in particular when it is made out of a material undergoing a phase transition (e.g. Nitinol) at body temperature.

With classical delivery devices, the operator does not have the possibility to step backwards when he realizes that, for some reason, the stent is not perfectly at its right place.

On the contrary, remote-activated retaining means 20 that are part of the device 1 according to the invention provides for a very firm grasp on the stent 7, allowing the inner tube 8 to be slided back relative to the outer sheath 16 up to the initial (closed) position of the chamber 6, even when the stent 7 has been previsously deployed up to 80% of its length.

Thanks to the retaining means 20, it has become possible to re-position the stent 7 in a more adequate position, either after an axial displacement, or after a rotation as the case may be.

Figure 3:
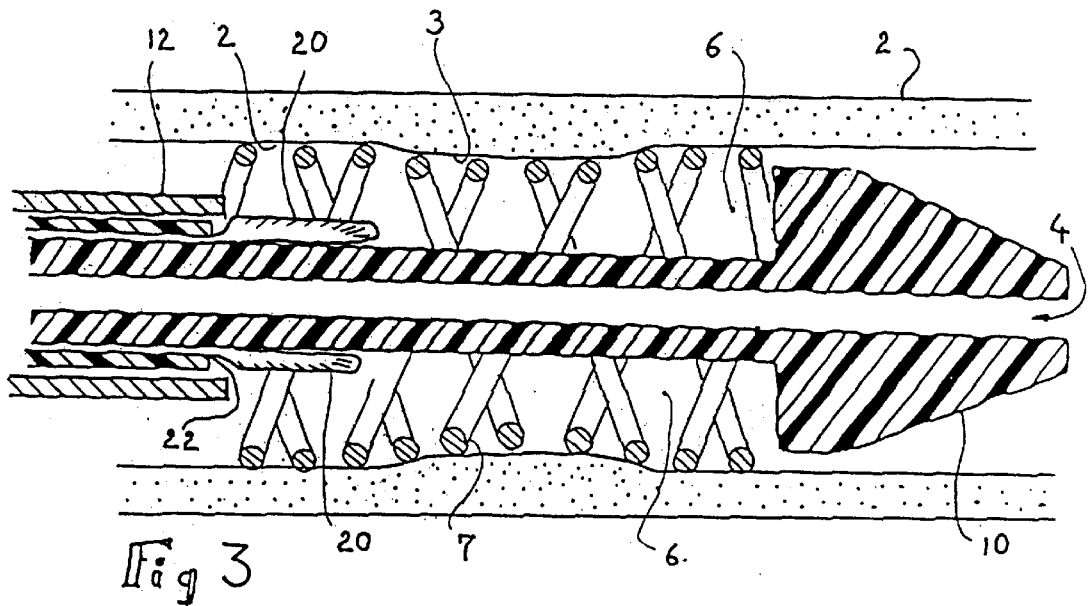
FIG. 3 is a diagrammatic view of the device of FIGS. 1, 2 at a later stage of the deployment operation.

When the stent 7 has been given its correct position, the retaining device 20 can be deflated and the outer sheath 16 is pulled fully backwards, as represented on FIG. 3.

Figure 4:
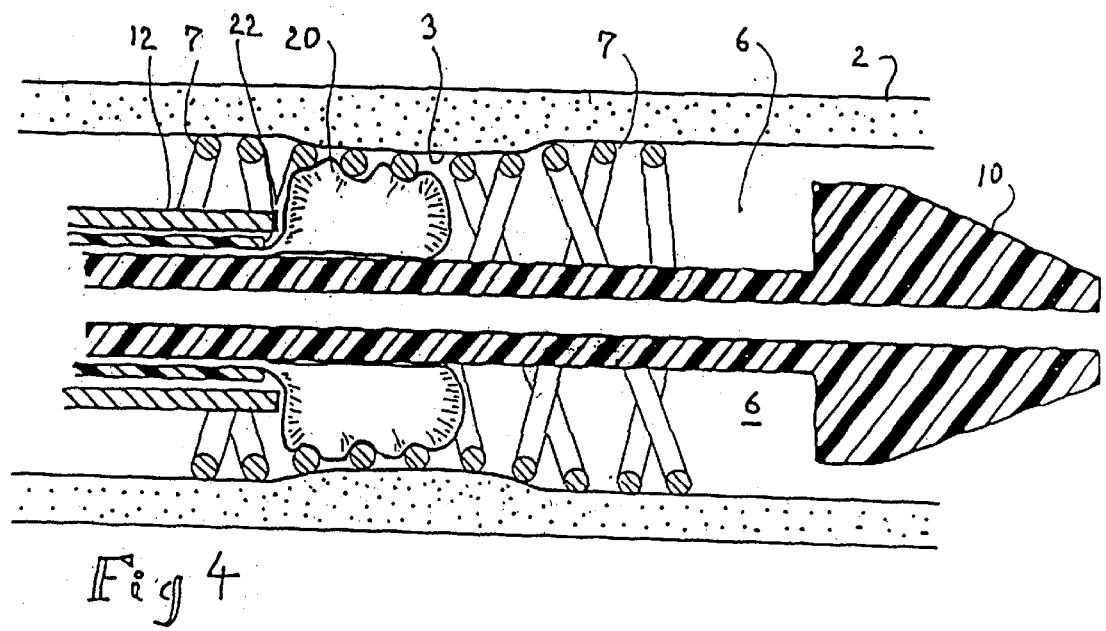
FIG. 4 is a diagrammatic view of a possible use of a device according to FIG. 1 after complete release of a stent.

The device 1 of the invention can then be removed through the expanded stent 7 or, as can be seen from FIG. 4, it can provide for a further advantageous step.

If the control screen reveals that the operation has not been absolutely successful (e.g., as shown on FIG. 3, when the stenosis 2 prevents the stent 7 from fully expanding), it remains possible, without removing the device 1, to further use the retaining micro-balloon 20, acting now, as a classical dilatation balloon, by moving the entire device 1 forwards and inflating the micro-balloon 20 again, this time at a pressure sufficient for it to reach the diameter of the vessel 2 to be cured. The use of the present device 1 thus allows a precious gain on the time spent for the operation and on the pain the patient has to endure.

The pressure required to inflate the micro-balloon 20 is exerted by a fluid carried along a second lumen 22 extending along the axial lumen 4 of the inner tube 8.

This inner tube 8 is preferably rigid, so as to avoid kinking during the introduction steps. PEEK (polyether ketone) or POM (polyacetol) are, inter alia, particularly suitable materials.

The inflatable balloon 20 must also be made of a rigid and not compliant material, but it can also be compliant so as to comply with the shape of the stent 7. It can be made out of PE or PET (Polyethylen or polyethylen terephtalate).

The external diameter and the length of the balloon 20 must be carefully chosen so as to avoid an excessive inflatation at its distal end, which could lead to refraining the stent 7 from being driven back into the chamber 6.

The outer sheath 16 must of course afford an excellent resistance to compression in order not to become distended by the stent 7. The outer sheath 16 is preferably reinforced by a multiwire braiding 24 as shown in FIG. 5 and 6.

Here again, POM or PEEK or other organic materials are best suitable.

The driving fluid can be fed by a known inflation syringe connected to the second lumen 22 via a known Y-adapter (not shown).

Figure 5:
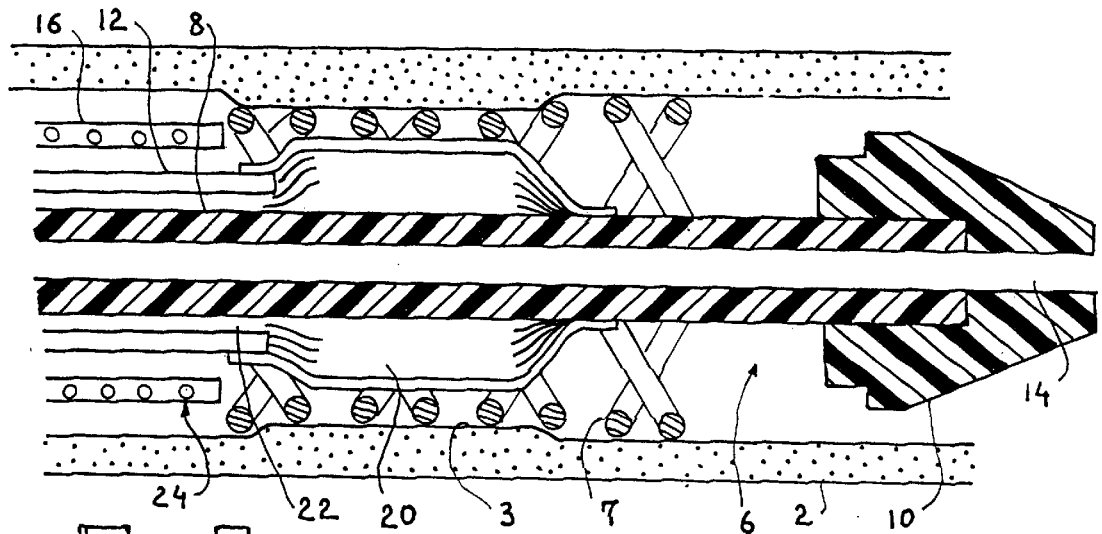
FIG. 5 is a diagrammatic view of another embodiment of the device at a stage corresponding to FIG. 3.
Figure 6:
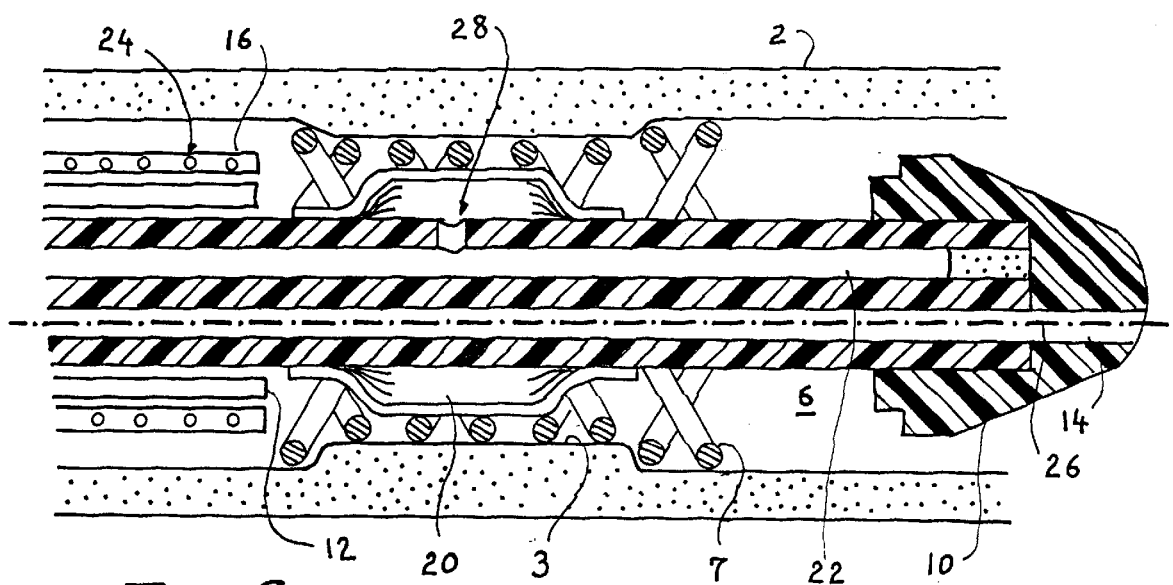
FIG. 6 is a diagrammatic view of still another embodiment at the same stage of deployment.

FIGS. 5 and 6 display two possible embodiments of the second lumen 22 and of the balloon 20. As can be seen on FIG. 5, the balloon 20 is fixed at its distal end to the inner tube 8 and, at its proximal end, of the peripheral side of the pusher 12, the second lumen extending between the inner tube 8 and the pusher 12.

FIG. 6 displays an embodiment wherein the inner tube 8 encloses two separated lumens. A first lumen 14 for passing the guide wire 26 is continued through the atraumatic tip 10. A second lumen 22 comprises at least one lateral outlet 28 communicating with the inner volume of the macro-balloon 20. This second lumen 22 is blocked up at its distal end, toward the atraumatic tip 10.

I claim:

1. A reversible-action endoprosthesis delivery device extending between a distal end and a proximal handling end, comprising:

an axially extending inner tube surrounded by an outer sheath, the inner tube and outer sheath forming, near a distal end of the inner tube, a chamber adapted to enclose a self-expandable endoprosthesis in a radially contracted state, the inner tube being axially movable relative to the outer sheath to open the chamber; and a remote-activated retaining device, disposed at a proximal end of the chamber, and being adapted to selectively retain or release a proximal end of the endoprosthesis when the chamber is partially opened.

2. A delivery device according to claim 1 wherein the remote-activated retaining means comprises an inflatable balloon fixed to the inner tube, this balloon being connected to pressure means placed at the proximal end of the delivery device.

3. A delivery device according to claim 2 wherein the inflatable balloon is placed near the proximal part of the chamber.

4. A delivery device according to claim 3, wherein the balloon is able to be inflated up to a diameter corresponding to the diameter of a body vessel.

5. A delivery device according to claim 2, wherein the balloon is able to be inflated up to a diameter corresponding to the diameter of a body vessel.

6. A delivery device according to claim 2, wherein the outer sheath is reinforced by a multiwire braiding.

7. A delivery device according to claim 6 wherein the braiding comprises metal wires.

8. A delivery device according to claim 1, wherein the outer sheath is reinforced by a multiwire braiding.

9. A delivery device according to claim 8 wherein the braiding comprises metal wires.

10. A delivery device according to claim 1, wherein the self-expandable endoprosthesis comprises a braid of shape-memory alloy.

11. A delivery device according to claim 1, wherein the retaining device is further adapted to draw the endoprosthesis back into the chamber after a portion of the endoprosthesis has been released from the chamber.

* * * * *